United States Patent
Essack et al.

(10) Patent No.: US 10,085,967 B2
(45) Date of Patent: Oct. 2, 2018

(54) TREATMENT OF SICKLE CELL DISEASE

(71) Applicant: KING ABDULLAH UNIVERSITY OF SCIENCE AND TECHNOLOGY, Thuwal (SA)

(72) Inventors: Megbubah Essack, Thuwal (SA); Vladimir Bajic, Thuwal (SA); Aleksandar Radovanovic, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 15/483,306

(22) Filed: Apr. 10, 2017

(65) Prior Publication Data

US 2017/0209412 A1    Jul. 27, 2017

Related U.S. Application Data

(62) Division of application No. 14/345,206, filed as application No. PCT/IB2012/002887 on Sep. 13, 2012, now Pat. No. 9,655,905.

(60) Provisional application No. 61/534,449, filed on Sep. 14, 2011.

(51) Int. Cl.
| | |
|---|---|
| *A61K 31/34* | (2006.01) |
| *A61K 31/365* | (2006.01) |
| *A61K 45/06* | (2006.01) |
| *A61K 31/551* | (2006.01) |

(52) U.S. Cl.
CPC .......... *A61K 31/365* (2013.01); *A61K 31/551* (2013.01); *A61K 45/06* (2013.01); *A61K 31/34* (2013.01)

(58) Field of Classification Search
CPC .................................................... A61K 31/34
USPC ....................................................... 514/461
See application file for complete search history.

(56) References Cited

U.S. PATENT DOCUMENTS

| | | |
|---|---|---|
| 5,399,363 A | 3/1995 | Liversidge et al. |
| 5,466,468 A | 11/1995 | Schneider et al. |
| 5,543,158 A | 8/1996 | Gref et al. |
| 5,580,579 A | 12/1996 | Ruddy et al. |
| 5,641,515 A | 6/1997 | Ramtoola |
| 5,725,871 A | 3/1998 | Illum |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 6,613,308 B2 | 9/2003 | Bartus et al. |
| 6,737,514 B1 | 5/2004 | Wang et al. |
| 2007/0185045 A1 | 8/2007 | Ratcliffe |

FOREIGN PATENT DOCUMENTS

WO    WO-2004106325 A1    12/2004

OTHER PUBLICATIONS

Charache et al., "Treatment of sickle cell anemia with 5-azacytidine results in increase fetal hemoglobin production and is associated with nonrandom hypomethylation of DNA around the γ-α-β-globin gene complex", The Proceeding of the National Academy of Sciences of the USA, vol. 80, No. 15, pp. 4842-4846 (1983).*
Chokchaisiri et al., "Labdane Diterpenes for the Aerial Parts of Curcuma comosa Enhance Fetal Hemoglobin Production in an Erythroid Cell Line", Journal of Natural Products, vol. 73, No. 4, pp. 724-728 (2010).*
Fibach et al., "Enhanced Fetal Hemoglobin Production by Phenylacetate and 4-Phenylbutyrate in Erythroid Precursors Derived From Normal Donors and Patients With Sickle Cell and β-Thalassemia", Blood, vol. 82, No. 7, pp. 2203-2209 (1993).*
Chokchaisiri et al., "Labdane diterpenes from the aerial parts of Curcuma comosa enhance fetal hemoglobin production in an erythroid cell line", Journal of Natural Products, Apr. 23, 2010, vol. 73, No. 4, pp. 724-728.
Cokic et al., "Hydroxyurea induces fetal hemoglobin by the nitric oxide-dependent activation of soluble guanylyl cyclase", J Clin Invest, 2003, vol. 111, pp. 231-239.
Olnes et al, "Improvement in hemolysis and pulmonary arterial systolic pressure in adult patients with sickle cell disease during treatment with hydroxyurea" Am J Hematol, Aug. 2009, vol. 84. No. 8, pp. 530-532.
Brawley et al., "National Institutes of Health Consensus Development Conference Statement: Hydroxyurea Treatment for Sickle Cell Disease", Ann Intern Med, Jun. 17, 2008, vol. 148, No. 12., pp. 932-938.
Haynes et al., "Hydroxyurea attenuates activated neutrophil-mediated sickle erythrocyte membrane phosphatidylserine exposure and adhesion to pulmonary vascuiar endothelium", American Journal of Physiology—Heart and Circulatory Physiology, Jan. 1, 2008, vol. 294, No. H379-H385.
Abraham et al., "Asymmetric synthesis of N,O,O,O-tetra-acetyl d-lyxo-phytosphingosine, jaspine B (pachastrissamine), 2-epi-jaspine B, and deoxoprosophylline via lithium amide conjugate addition", Org. Biomol. Chem., 6:1665-1673, 2008.
Arita et al., "Rho kinase inhibition by fasudii ameliorates diabetes-induced microvascular damage", Diabetes, 58:215-226, 2009.
Barabino et al., "Sickle cell biomechanics", Annu. Rev. Biomed. Eng., 12:345-367, 2010.
Belcher et al., "Heme oxygenase-1 is a modulator of inflammation and vaso-occlusion in transgenic sickle mice", J. Clin. Invest., 116:808-816, 2006.
Bernaudin et al., "Long-term results of related myeloablative stem-cell transplantation to cure sickle cell disease", Blood 110:2719-2756, 2007.

(Continued)

*Primary Examiner* — Kevin E Weddington
(74) *Attorney, Agent, or Firm* — Pabst Patent Group LLP

(57) ABSTRACT

The present invention includes embodiments for treatment and/or prevention of sickle cell disease that employ Hydroxyfasudil or Isocoronarin D alone or either in conjunction with each other or an inducer of HbF production. The compounds may act synergistically, and the compounds employed circumvent the side effects seen with Hydroxyurea.

3 Claims, No Drawings

(56) References Cited

OTHER PUBLICATIONS

Bianchi et al., "Fetal Hemoglobin Inducers from the Natural World: A Novel Approach for Identification of Drugs for the Treatment of β-Thalassemia and Sickle-Cell Anemia", eCAM, 6(2):141-151, 2007.

Canalli et al., "Participation of Mac-1, LFA-1 and VLA-4 integrins in the in vitro adhesion of sickle cell disease neutrophils to endothelial layers, and reversal of adhesion by simvastatin", Haematologica. 96:526-533, 2011.

Chada et al., "The synergy site of fibronectin is required for strong interaction with the platelet integrin αIIbβ3", Ann. Biomed. Eng., 34:1542-1552, 2006.

Charache et al., "Hydroxyurea and sickle cell anemia. Clinical utility of a myelosuppressive 'switching' agent. The Multicenter Study of Hydroxyurea in Sickle Cell Anemia", Medicine (Baltimore), 75:300-326, 1996.

Chiu et al., "Shear stress increases ICAM-1 and decreases VCAM-1 and E-selectin expressions induced by tumor necrosis factor-[alpha] in endothelial cells", Arterioscler Thromb Vasc. Biol., 24:73-79, 2004.

Conran et al., "Increased soluble guanylate cyclase activity in the red blood cells of sickle cell patients", Br. J. Haematol., 124:547-554. 2004.

Conran et al., "Leukocyte numbers correlate with plasma levels of granulocyte-macrophage colony-stimulating factor in sickle cell disease", ann. Hematol., 86:255-261, 2007.

Croizat, "Circulating cytokines in sickle cell patients during steady state", Br. J. Haematol, 87:592-597, 1994.

Dai et al., "Attenuation of pulmonary hypertension secondary to left ventricular dysfunction in the rat by Rho-kinase inhibitor fasudil". Pediatr Pulmonol., 46:45-59, 2011.

Devi et al., "Platelet recruitment to the inflamed glomerulus occurs via an αIIbβ3/GPVI-dependent pathway", Am. J. Pathol., 177:1131-1142. 2010.

Ding et al., "Fasudil protects hippocampal neurons against hypoxia-reoxygenation injury by suppressing microglial inflammatory responses in mice", J. Neurochem., 114:1619-1629, 2010.

Eberhardt et al., "Sickle cell anemia is associated with reduced nitric oxide bioactivity in peripheral conduit and resistance vessels", Am. J. Hematol, 74:104-111, 2003.

Ergul et al., "Vasoactive factors in sickle cell disease: in vitro evidence for endothelin-1-mediated vasoconstriction", Am. J. Hematol, 78:245-251, 2004.

Ferry et al., "Globin gene silencing in primary erythroid cultures. An inhibitory role for interleukin-6", J. Bio. Chem., 272:20030-20037, 1997.

Frenette, Sickle cell vaso-occlusion: multistep and multicellular paradigm, Curr Opin. Hematol., 9:101-106, 2002.

Frenette and Atweh, "Sickle cell disease: old discoveries, new concepts, and future promise", J. Clin. Invest., 117:850-858, 2007.

Friedrisch et al., "DNA damage in blood leukocytes of individuals with sickle cell disease treated with hydroxyurea", Mutat Res., 649:213-220, 2008.

Galley and Webster, "Physiology of the endothelium", Br. J. Anaesth., 93:105-113, 2004.

Gambari and Fibach, "Medicinal Chemistry of Fetal Hemoglobin Inducers for Treatment of β-Thalassemia". Curr. Medic. Chem., 14:199-212, 2007.

Gambero et al., "Therapy with hydroxyurea is associated with reduced adhesion molecule gene and protein expression in sickle red cells with concomitant reduction in adhesive properties", Eur. J. Haematol. 78:144-151. 2007.

Grigg, "Effect of hydroxyurea on sperm count, motility and morphology in adult men with sickle cell or myeloproliferative disease", Intern Med. J., 37:190-192, 2007.

Hidalgo et al., "Heterotypic interactions enabled by polarized neutrophil microdomains mediate theromboinflammatory injury", Nat. Med., 15:384-391, 2009.

Huang et al., "Potentiation of taxol efficacy and by discodermolide in ovarian carcinoma xenograft-bearing mice", Clin. Cancer Res., 12:298-304, 2006.

Huang et al., "The total synthesis of psymberine", Org. Lett., 9:2597-2600. 2007.

Ingram, "Gene mutations in human hÆmoglobin: the chemical difference between normal and sickle cell hÆmoglobin", Nature, 180:326-328, 1957.

Kaul et al., "Anti-inflammatory therapy ameliorates leukocyte adhesion and microvascular flow abnormalities in transgenic sickle mice", Am. J. Physiol Heart Circ. Physiol., 287:H293-301, 2004.

Kim et al., "A novel roe of hypoxia-inducible factor in cobalt chloride- and hypoxia-mediated expression of IL-8 chemokine in human endothelial cells", J Immunol, 177:7211-7224, 2006.

Lanaro et al., "Altered levels of cytokines and inflammatory mediators in plasma and leukocytes of sicle cell anemia patients and effects of hydroxyurea therapy", J. Leukoc Biol, 85:235-242, 2009.

Lapoumeroulie et al., "Decreased plasma endothelin-1 levels in children with sickle cell disease treated with hydroxyurea", Haematologica, 90:40-403. 2005.

Lee et al., "Biologically active CD40 ligand is elevated in sickle cell anemia: potential role for platelet-mediated inflammation", Arterioscler Thromb Vasc. Biol., 26:1626-1631, 2006.

Ley et al., "5-Azacytidine increases gamma-globin synthesis and reduces the proportions of dense cells in patients with sickle cell anemia", Blood, 62:370-380, 1983.

Lin et al., "Activation of p38 MAPK by damnacanthal mediates apoptosis in SKHep 1 cells through the DR5/TRAIL and TNFR1/TNF-alpha and p53 pathways", Eur. J. Pharmacol., 650:120-129, 2011.

Lockamy et al., "Urease enhances the formation of iron nitrosyl hemoglobin in the presence of hydroxyurea", Biochim Biophys. Acta. 1622:109-116, 2003.

Lomakina and Waugh, "Signaling and Dynamics of Activation of LFA-1 and Mac-1 by Immobilized IL-8", Cell Mol. Bioen., 3:106-116, 2010.

Makis et al., "Circulating endothelin-3 levels in patients with sickle cell disease during hydroxyurea treatment", Haematologica. 89:360-361, 2004.

Miguel et al., "Inhibition of phosphodiesterase 9A reduces cytokine-simulated in vitro adhesion of neutrophils from sickle cell anemia individuals", Inflamm. Res., 2011.

Modell and Darlison, "Global epidemiology of haemoglobin disorders and derived service indicators", Bull World Health Organ., 86:480-487, 2008.

Mozzarelli et al., "Delay time of hemoglobin S polymerization prevents most cells from sickling in vivo", Science, 237:500-506, 1987.

Musa et al., "Pattern of serum cytokine expression and T-cell subsets in sickle cell disease patients in vaso-occlusive crisis", Clin Vaccine Immunol. 17:602-608, 2010.

Nath et al., "Transgenic sickle mice are markedly sensitive to renal ischemia-reperfusion injury", Am. J. Pathol., 166:963-972, 2005.

Oh et al., "Platelet-activating factor in plasma of patients with sickle cell disease in steady state", J. Lab. Clin. Med., 130:191-169, 1997.

Osarogiagbon et al., "Reperfusion injury pathophysiology in sickle transgenic mice", Blood, 96:314-320, 2000.

Otterbein et al., "Heme oxygenase-1: unleashing the protective properties of heme", Trends Immuno., 24:449-455, 2003.

Phelan et al., "Sickle erythrocytes, after sickling, regulate the expression of the endothelin-1 gene and protein in human endothelial cells in culture", J. Clin. Invest., 96:1145-1151, 1995.

Radi et al., "Peroxynitrite-induced membrane lipid peroxidation: the cytotoxic patential of superoxide and nitric oxide", Arch biochem. Biophys, 288:481-487, 1991.

Rajan et al., "NF-kappaB, but not p38 MAP kinase, is required from TNF-alpha-induced expression of cell adhesion molecules in endothelial cells", J. Cell Biochem, 105:477-486, 2008.

Reiter and Gladwin, "An emerging role for nitric oxide in sickle cell disease vascular homeostatis and therapy", Curr. Opin. Hematol., 10:99-107, 2003.

Remington's Pharmaceutical Science, 18th Ed. Mack Printing Company, 1990.

(56) References Cited

OTHER PUBLICATIONS

Sadelain, "Recent advances in globin gene transfer for the treatment of beta-thalassemia and sickle cell anemia", Curr. Opin. Hematol., 13:142-148, 2006.
Saleh et al., "Levels of endothelial, neutrophil and platelet-specific factors in sickle cell anemia patients during hydroxyurea therapy", Acta Haematol, 102:31-37, 1999.
Santen et al., "Rho-kinase signaling regulates CXC chemokine formation and leukocyte recruitment in colonic ischemia-reperfusion", Int. J. colorectal Dis., 25:1063-1070, 2010.
Satoh et al., "Amelioration of endothelial damage/dysfunction is a possible mechanism for the neuroprotective effects of Rho-kinase inhibitors against ischemic brain damage", Brain Res Bull, 81:191-195, 2010.
Segers et al., "Mesenchymal stem cell adhesion ot cardiac microvasular endothelium activators and mechanisms", Am. J. Physiol Heart Physiol, 290:H1370-1377, 2006.
Shiotani et al., "Involvement of Rho-kinase in cold ischemia-reperfusion injury after liver transplant in rats", Transplatation, 78:375-382, 2004.
Skarpidi et al., "Novel in vitro assay for the detection of pharmacologic inducers of fetal hemoglobin", Blood, 96:321. 2000.
Solovey et al., "Tissue factor expression by endothelial cells in sickle cell anemia", J. Clin. Invest., 101:1899-1904, 1998.
Solovey et al., "Endothelial nitric oxide synthase and nitric oxide regulate endothelial tissue factor expression in vivo in the sickle transgenic mouse", Am. J. Hematol., 85:41-46, 2010.
Solovey et al., "Circulating activated endothelial cells in sickle cell anemia", N. Engl. J. Med., 337:1584-1590, 1997.
Steinberg, "Sickle cell anemia, the first molecular disease: overview of molecular etiology, pathophysiology, and therapeutic approaches", Scientific World Journal, 8:1295-1324. 2008.
Sultana et al., "Interaction of sickle erythrocytes with endothelial cells in the presence of endothelial cell conditioned medium induces oxidant stress leading to transendothelial migration of monocytes", Blood, 92:3924-3935. 1998.
Takata et al., "Fasudil-induced hypoxia-inducible factor-1α degradation disrupts a hypoxia-driven vascular endothelial growth factor autocrine mechanism in endothelial cells", Mol. Cancer Ther., 7:1551-1561. 2008.
Taylor et al., "Effect of anti-IL-6 and anti-10 monolonal antibodies on the suppression of the normal T lymphocyte mitogenic response by steady state sickle cell disease sera", Immunol. Invest., 30:209-219, 2001.
Thomas et al., "Marine drugs from sponge-microbe association—a review", Mar. Drug, 8:1417-1468. 2010.
Tsukamoto et al., "Naamidines H and I, cytotoxic imidazole alkaloids from the Indonesian marine sponge *Leucetta chagosensis*", J. Nat. Prod., 70:1658-1660, 2007.
Turhan et al., "Primary role for adherent leukocytes in sickle cell vascular occlusion: a new paradigm", Proc. Natl. Acad. Sci. USA, 99:3047-3051, 2002.
Vadolas et al., "Cellular genomic reporter assays for screening and evaluation of inducers oft fetal hemoglobin", Human Molecular Genetics, 13(2):223. 2004.

Van Gils et al., "Molecular and functional interactions among monocytes, platelets, and endothelial cells and their relevance for cardiovascular diseases", J Leukoc Biol., 85:195-204, 2009.
Vilas-Boas et al., "Arginase levels and their association with Th17-related cytokines, soluble adhesion molecules (sICAM-1 and sVCAM-1) and hemolysis markers among steady-state sickle cell anemia patients", Ann. Hematol., 89:877-882. 2010.
Wanderer, "Rationale for IL-1beta targeted therapy for ischemia-reperfusion induced pulmonary and other complications in sickle cell disease", J. Pediatr. Hematol. Oncol., 31:537-538, 2009.
Werdehoff et al., "Elevated plasma endothelin-1 levels in sickle cell anemia: relationships to oxygen saturation and left ventricular hypertrophy", Am. J. Hematol., 58:195-199, 1998.
Westwick et al., Platelet activation during steady state sickle cell disease, J. Med., 14:17-36, 1983.
Wun et al., "Activated monocytes and platelet-monocyte aggregates in patients with sickle cell disease", Clin. Lab Haematol., 24:81-88, 2002.
Wun et al., "Platelet-erythrocyte adhesion in sickle cell disease", J. Investig. Med., 47:121-127, 1999.
Yoong et al., "Markers of platelet activation, thrombin generation and fibrinolysis in women with sickle cell disease: effects of differeing forms of hormonal contraception", Eur. J. Haematol., 70:310-314, 2003.
Rees et al., "Sickle-cell disease", Lancet, 376:2018-2031, 2010.
He et al., "Antiinflammatory effect of Rho kinase blockade via inhibition of NF-kapa B activation in rheumatoid arthritis", Arthritis Rheum, 58:3366-3376. 2008.
Advani et al., "Long-Term Administration of the Histone Deacetylase Inhibitor Vorinostat Attenuates Renal Injury in Experimental Diabetes through an Endothelial Nitric Oxide Synthase-Dependent Mechanism", Am. J. Pathol., 178:2205-2214, 2011.
Choo et al., "Histone deacetylase inhibitors MS-275 and SAHA induced growth arrest and suppressed lipopolysaccharide-stimulated NF-κB p65 nuclear accumulation in human rheumatoid arthritis synovial fibroblastic E11 cells", Rheumatoology (Oxford), 49:1447-1460, 2010.
Niihara et al., "L-glutamine therapy reduces endothelial adhesion or sickle red blood cells to human umbilical vein endothelial cells". BMC Blood Disorders, 5:4, 2005.
Cavalli-Sforza et al., "The history and geography of human genes", New Jersey, 1994.
Kato et al., "Levels of soluble endothelium-derived adhesion molecules in patients with sickle cell disease are associated with pulmonary hypertension, organ dysfunction, and mortality", Br. J. Haematol., 130:943-953, 2005.
Singh et al., "(+)-14β-Hydroxylabda-8(17),12-dieno-16,15-lactone [(+)-Isocoronarin-D]: a New Diterpene From *Hedychium coronarium* (Zingiberaceae)", Aust. J. Chem. 44:1789, 1991.
Bradley et al., "Vorinostat in advanced prostate cancer patients progressing on prior chemotherapy (National Cancer Institute Trial 6862): v2011-001-030 Confidential 4 trial results and interleukin-6 analysis: a study by the Department of Defense Prostate Cancer Clinical Trial Consortium and University of Chicago Phase 2 Consortium", Cancer, 115:5541-5549. 2009.

* cited by examiner

TREATMENT OF SICKLE CELL DISEASE

This application claims priority to U.S. Provisional Patent Application Ser. No. 61/534,449, filed Sep. 14, 2011, which application is incorporated by reference herein in its entirety.

TECHNICAL FIELD

The field of the present invention includes at least biology, cell biology, and medicine. In particular aspects, the field of the present invention includes treatment and/or prevention of a blood disorder, such as sickle cell disease.

BACKGROUND OF THE INVENTION

Sickle cell disease (SCD) is the most common life-threatening monogenic disorder in the world with statistics indicating that approximately 80% (230,000) of children affected globally are born in sub-Saharan Africa (Modell and Darlison 2008). SCD is a severe hemoglobinopathy that produces multisystem complications due to the expression of abnormal sickle hemoglobin (HbS). The most common type of SCD is sickle cell anemia (SCA) (also referred to as HbSS or SS disease or hemoglobin S) in which there is homozygosity for the mutation that causes HbS. The more rare types of SCD in which there is heterozygosity (one copy of the mutation that causes HbS and one copy for another abnormal hemoglobin allele) for the mutation include sickle-hemoglobin C (HbSC), sickle $\beta^+$ thalassemia (HbS/$\beta^+$) and sickle $\beta^0$ thalassemia (HbS/$\beta^0$).

Sickle cell disease (SCD) can arise from a single point mutation that causes erythrocyte deformation or sickle-shaped erythrocytes (Ingram 1957). Sickled-shaped erythrocytes are associated with clinical manifestations of SCD, such as anemia, recurrent painful vaso-occlusive episodes, infections, acute chest syndrome, pulmonary hypertension, stroke, priapism, osteonecrosis, renal insufficiency, leg ulcers, retinopathies, and cardiac disease (Frenette and Atweh 2007, Steinberg 2008).

Pathophysiology

Sickle-shaped Erythrocytes

SCD arises from a single point mutation (GAG>GTG) in codon 6 of the HBB globin gene. This point mutation (GAG>GTG) results in the polar hydrophilic molecule, glutamic acid being substituted with the non-polar hydrophobic molecule, valine ($\beta^6$ Glu→Val) (Ingram 1957). The deoxygenated venous circulation causes the hydrophobic valine residue to associate with hydrophobic regions of adjacent molecules (Mozzarelli, et al 1987). This process of self-assembly (polymerization) generates the sickled hemoglobin molecule (HbS) that damages the membrane and cytoskeleton of the erythrocyte. The HbS repetitively enter into sickling and unsickling cycles incrementally increasing the damage to the erythrocyte membrane (Ischemia-reperfusion (IR) injury) resulting in irreversibly sickle-shaped erythrocytes (Barabino, et al 2010).

C-reactive protein (CRP) (Nath, et al 2005) and the markers of oxidative stress, such as xanthine oxidase (XO), salicylate hydroxylation and expired ethane, are significantly increased following IR injury (Huang, et al 2007, Osarogiagbon, et al 2000). The activation of XO and reduced Tetrahydrobiopterin (BH$_4$) levels in endothelial cells leads to increased reactive oxygen species (ROS) formation, which in turn leads to endothelial nitric oxide synthase (eNOS) uncoupling and further production of superoxide (Thomas, et al 2010). ROS causes endothelial cell membrane lipid peroxidation, inactivation of nitric oxide (NO), activation of nuclear factor of kappa light polypeptide gene enhancer in B-cells 1 (NF-κB) and Src/MAP kinase signaling, and induces production of tissue factor (TF), interleukin 8 (IL-8), and surface adhesion molecule expression (Belcher, et al 2006, Radi, et al 1991, Thomas, et al 2010). Thus, the ensuing oxidative stress contributes to hemolysis, inactivation of NO, and erythrocyte, leukocyte and platelet adhesive properties (Kaul, et al 2004, Sultana, et al 1998, Vilas-Boas, et al 2010).

The Sickled-shaped erythrocytes together with endothelial cells, activated leukocytes, platelets and plasma proteins participate in the multistep vaso-occlusion process (Frenette 2002).

TABLE 1

Ischemia-reperfusion (IR) injury-related molecules in individuals with SCD

| IR injury-related molecules | Expression status in SCD | References |
| --- | --- | --- |
| Xanthine oxidase (XO) | Up | (Osarogiagbon, et al 2000) |
| Tetrahydrobiopterin (BH$_4$) | Down | (Thomas, et al 2010) |
| C-reactive protein (CRP) | Up | (Nath, et al 2005) |
| Reactive Oxygen Species (ROS) | Up | (Huang, et al 2007) |

Endothelial Cells

Vascular homeostasis is harmonized by the endothelial cell vasoregulators regulating blood flow, growth of vascular smooth muscle cells and local inflammation (Huang, et al 2006). Endothelial cells are the primary producers of the major vasodilator, nitric oxide (NO) and prostacyclin, as well as vasoconstrictors such as endothelin, angiotensin II and prostaglandins (Galley and Webster 2004). These endothelial cell vasoregulators are characteristically imbalanced in individuals with SCD, resulting in endothelial dysfunction that contributes to vaso-occlusion process.

SCD is characterized by a reduced bioavailability of NO, due to 1/cell-free plasma hemoglobin and increased arginase activity encouraging hemolysis-related scavenging of NO (Reiter and Gladwin 2003), and 2/eNOS function being diminished due to a decrease in the nitric oxide synthase (NOS) substrate, arginine's ability to dimerize thereby contributing to reduced NO synthesis (Lin, et al 2011). The reduced NO decreases the NO-dependent vaso-dilation, contributing to an increase in vasoconstrictors such as endothelin-1 (ET-1) (Ergul, et al 2004, Werdehoff, et al 1998) and endothelin-3 (ET-3) (Makis, et al 2004). It has been demonstrated that Endothelin-3 induces endothelial cell interleukin 6 (IL-6) expression thereby mediating inflammation. Thus, IL-6 is also characteristically found to be increased in SCD patients (Makis, et al 2004).

TABLE 2

Endothelial cell vasoregulators that is imbalanced in individuals with SCD

| Endothelial Cell Vasoregulators | Type of Vasoregulator | Expression status in SCD | References |
| --- | --- | --- | --- |
| Nitric Oxide | vasodilator | down | (Eberhardt, et al 2003) |
| Endothelin-1 | vasoconstrictor | up | (Werdehoff, et al 1998) |
| Endothelin-3 | vasoconstrictor | up | (Makis, et al 2004) |

Activators of endothelial cells include NFκB (Belcher, et al 2005), hypoxia-inducible factor-1 (HIF-1) (Kim, et al 2006), ET-1 (Phelan, et al 1995) and TF (Solovey, et al 1998). Interestingly, it has been demonstrated that eNOS modulates the expression of TF by down-regulates it, however, eNOS is characteristically down-regulated in SCD patients (Solovey, et al 2010). Once activated, the endothelium produces cytokines such as tumour necrosis factor alpha (TNFα) (Lanaro, et al 2009) and interleukin 1 beta (IL-1β) (Croizat 1994, Wanderer 2009), chemokines and/or inflammatory molecules such as granulocyte macrophage-colony stimulating factor (GM-CSF) (Conran, et al 2007), IL-8 (Lanaro, et al 2009), IL-6 (Croizat 1994), interleukin 3 (IL-3) (Croizat 1994), interleukin 4 (IL-4) (Musa, et al 2010), and platelet activating factor (PAF) (Oh, et al 1997), and adhesion molecules such as vascular cell adhesion molecule 1 (VCAM-1), intercellular cell adhesion molecule 1 (ICAM-1), selectin E (SELE) and selectin P (SELP) (Chiu, et al 2004, Solovey, et al 1997). Rajan et al. demonstrated that NFκB is required for TNFα-induced expression of VCAM-1, ICAM-1 and SELE in endothelial cells (Rajan, et al 2008). The production of these inflammatory mediators and cell adhesion molecules is perpetuated by TNFα and IL-1β being potent activators of the endothelium (Segers, et al 2006). Heme oxygenase-1 (HO-1) (Belcher, et al 2006) and interleukin 10 (IL-10) (Musa, et al 2010) are characteristically found to be increased in SCD patients in an attempt to counteract the induced inflammation. HO-1 breaks down heme released during hemolysis thereby limiting oxidative stress and inflammation (Otterbein, et al 2003), whilst IL-10 limits the production of the pro-inflammatory cytokines (Lanaro, et al 2009, Taylor, et al 2001).

TABLE 3

Endothelial cell activation-related molecules in individuals with SCD

| Molecules | Types of Molecules | Expression status in SCD | References |
|---|---|---|---|
| NFκB | Activator of endothelial cells | up | (Belcher, et al 2005) |
| ET-1 | Activator of endothelial cells | up | (Phelan, et al 1995) |
| HIF-1 | Activator of endothelial cells | up | (Kim, et al 2006) |
| TF | Activator of endothelial cells | up | (Solovey, et al 1998) |
| eNOS | Inhibitor of endothelial cell activation | down | (Solovey, et al 2010) |
| TNFα | cytokine/inflammatory | up | (Lanaro, et al 2009) |
| IL-1β | cytokine/inflammatory | up | (Wanderer 2009) |
| IL-8 | chemokine/inflammatory | up | (Lanaro, et al 2009) |
| IL-4 | chemokine | up | (Musa, et al 2010) |
| PAF | chemokine | up | (Oh, et al 1997) |
| IL-6 | chemokine/inflammatory | up | (Croizat 1994) |
| GM-CSF | inflammatory | up | (Conran, et al 2007) |
| IL-3 | inflammatory | up | (Croizat 1994) |
| VCAM-1 | adhesion | up | (Solovey, et al 1997) |
| ICAM-1 | adhesion | up | (Solovey, et al 1997) |
| SELP | adhesion | up | (Solovey, et al 1997) |
| SELE | adhesion | up | (Solovey, et al 1997) |

Leukocytes

The sickled erythrocytes stimulates leukocyte recruitment: ensuing the inflammatory stimulus, leukocytes are recruited to the activated endothelium of the venous circulation where it forms adhesive interactions with the activated endothelium and sickled erythrocytes, leading to a reduced blood flow and eventually vaso-occlusion (Turhan, et al 2002).

SCD patients characteristically have increased levels of activated leukocytes. It has been demonstrated that SCD-related leukocytes have increased expression and activity of the integrin, beta 2 (complement component 3 receptor 3 and 4 subunit) (ITGB2) LFA-1, integrin, alpha M (complement component 3 receptor 3 subunit) (ITGAM) and integrin, beta 1
(fibronectin receptor, beta polypeptide, antigen CD29 includes MDF2, MSK12) (ITGB1) in the presence of the inflammatory stimulus, IL-8 (Canalli, et al 2011, Lomakina and Waugh 2010). These SCD leukocyte integrins have been demonstrated to ligate with endothelial ICAM-1 (Canalli, et al 2011) and fibronectin 1 (FN1) (Miguel, et al 2011). The leukocyte recruitment process is enhanced by the overexpression SELP and SELE in endothelial cells as endothelial cells lacking SELP and SELE have demonstrated reduced leukocyte recruitment and diminished vaso-occlusion (Turhan, et al 2002). Additionally, the lack of SELE has also been demonstrated to reduce the adhesion of sickled erythrocytes to leukocytes (Hidalgo, et al 2009).

TABLE 4

Leukocyte activation-related molecules in individuals with SCD

| Molecules | Types of Molecules | Expression status in SCD | References |
|---|---|---|---|
| ITGB2 | leukocyte integrin | up | (Canalli, et al 2011) |
| ITGAM | leukocyte integrin | up | (Canalli, et al 2011) |
| ITGB1 | leukocyte integrin | up | (Canalli, et al 2011) |

Platelets

SCD plateles show increased surface expressions of SELP, activated $\alpha_{IIb}\beta_3$ (GPIIbIIIa) (Devi, et al 2010) and higher concentrations of the platelet activation markers, platelet factor 4 (PF-4) and β thromboglobulin (TGB) (Westwick, et al 1983, Yoong, et al 2003). Activated platelets have been shown to release endothelium activators, such as soluble CD40 ligand (sCD40L) (Lee, et al 2006), PF-4 (Westwick, et al 1983) and IL-1β (Wun, et al 2002). In healthy individuals, platelet adhesion is inhibited by the antithrombotic factor, NO whilst SCD platelet adhesion is stimulated by the activated endothelium releasing ADP, TF, von Willebrand factor (vWF) and the expression of platelet-binding adhesion molecules such as glycoprotein Ib (platelet), beta polypeptide (GPIb), selectin P ligand (SELPLG), vitronectin receptor (VTNR) and ICAM-1 (van Gils, et al 2009). SCD platelets have been demonstrated to have increased adhesion to the αIIbβ3 platelet integrin ligand, fibrinogen that in turn favors the adhesion of platelets to endothelium protein FN1 (Chada, et al 2006). Moreover, platelets and sickled erythrocytes have been demonstrated to aggregate via the formation of thrombospondin bridges thereby contributing to vaso-occlusion (Wun, et al 1999).

TABLE 5

Platelet activation-related molecules in individuals with SCD

| Molecules | Type of molecule | Expression status in SCD | References |
|---|---|---|---|
| $\alpha_{IIb}\beta_3$ | platelet activation | up | (Devi, et al 2010) |
| PF-4 | platelet activation/ endothelium activators | up | (Westwick, et al 1983) |
| TGB | platelet activation | up | (Yoong, et al 2003) |
| sCD40L | endothelium activators | up | (Lee, et al 2006) |
| IL-1β | endothelium activators | up | (Wun, et al 2002) |

TABLE 5-continued

Platelet activation-related molecules in individuals with SCD

| Molecules | Type of molecule | Expression status in SCD | References |
|---|---|---|---|
| GPIb | adhesion | up | (van Gils, et al 2009) |
| PSGL-1 | adhesion | up | (van Gils, et al 2009) |
| VTNR | adhesion | up | (van Gils, et al 2009) |
| ICAM-1 | adhesion | up | (van Gils, et al 2009) |
| fibrinogen | platelet integrin ligand | up | (Chada, et al 2006) |

Hydroxyurea

Hydroxyurea (HU) is a FDA approved drug that is the only current treatment proven to modify the disease process of SCD (Brawley, et al 2008). HU positively counteracts the pathophysiology of SCD by increasing the production of fetal hemoglobin (HbF)-containing erythrocytes via stimulation of the NO-cyclic guanosine monophosphate (cGMP) signaling pathway (Cokic, et al 2003) and indirectly altering gene expression and proteins associated with the pathophysiology of SCD. The increased concentration of HbF-containing erythrocytes dilutes the concentration of sickled erythrocytes, thereby sequentially triggering decreased hemolysis (Olnes, et al 2009), increased NO bioavailability (Conran, et al 2004) and decreased endothelium activation (Haynes, et al 2008), which likely accounts probably accounts for the beneficial effects of HU treatment in SCD patients. However, HU has been demonstrated to reduce leukocyte counts in patients on therapy (Charache, et al 1996). Although HU improved clinical symptoms by reducing pain and vaso-occlusive crises, acute chest syndrome, transfusion requirements, and hospitalization, SCD patients treated with HU have demonstrated side effect such as inducing DNA damage (Friedrisch, et al 2008), reducing sperm counts (Grigg 2007) and producing iron nitrosyl Hb (Lockamy, et al 2003). There is a need in the art for improved SCD therapy that lacks one or more side effects of HU.

BRIEF SUMMARY OF THE INVENTION

The present invention is directed to methods and compositions associated with treatment and/or prevention of one or more blood disorders. Although in particular embodiments the blood disorder is SCD, in specific embodiments, one or more other blood disorders may be treated with the present invention: a bleeding disorder (including clotting disorders, hypercoagulability, hemophilia, or von Willebrand disease, for example), platelet disorder (essential or primary thrombocythemia or thrombocytopenia, for example), and/or hemophilia or anemia may be treated, for example. In particular embodiments of the invention, there are methods and compositions for treatment and/or prevention of sickle cell disease (which may be referred to as sickle-cell anaemia (or anemia; SCA) or drepanocytosis). The disease may be present in a male or female mammal. Mammalian and/or non-human mammals may be used as sickle cell models, in certain cases. The individual treated with methods and/or compositions of the invention may be experiencing vaso-occlusive crisis and/or acute chest crisis, in specific cases. In specific embodiments, the individual may be experiencing or may experience negative side effects of a drug, such as a drug that directly or indirectly results in increased coagulation and/or increased inflammation; in specific embodiments, the drug is HU.

Currently, Hydroxyurea (HU) is the only FDA approved drug capable of modifying the sickle cell disease (SCD) processes. However, due to side effects of HU there is a general interest for a less toxic drug for SCD. The inventors identified a drug (Hydroxyfasudil (also known as Fasudil)) for the treatment of SCD that is a more suitable treatment for SCD than the currently administered HU therapy. Hydroxyfasudil was identified by the inventors using an automated literature mining system that was then complemented by additional hand curation.

Hydroxyfasudil, a recognized Rho-kinase inhibitor, has been demonstrated to attenuate pulmonary hypertension secondary to left ventricular dysfunction that is characterized by increases in mean pulmonary arterial pressure, pulmonary arteriolar medial thickness, active RhoA, Rhokinase II, Rho-kinase activity, endothelial nitric oxide synthase (eNOS) and endothelin-1 (ET-1) concomitant with decreased levels in NO and cGMP in the lung. As mentioned before, the effectiveness of HU for the treatment of SCD is a consequence of its ability to produce HbF via stimulation of the NO-cyclic guanosine monophosphate (cGMP) signaling pathway (Cokic, et al 2003). Hydroxyfasudil induces increased levels of eNOS, NO and cGMP and in specific embodiments of the invention, Hydroxyfasudil produces HbF via stimulation of the NO-cyclic guanosine monophosphate (cGMP) signaling pathway as well (Dai, et al 2011). Additionally, IL-6 has been demonstrated to play an important role in globin gene silencing (Ferry, et al 1997), even though increased IL-6 levels have been associated with the pathophysiology of SCD. Hydroxyfasudil, on the other hand, has demonstrated the ability to reduce IL-6 levels after hypoxia/reoxygenation (H/R) injury in brain tissue (Ding, et al 2010), indicating that at least in some embodiments that it has ability to produce HbF.

HU has also been shown to change the clinical symptoms of SCD by decreasing the levels of vasoconstrictors such as ET-1 (Lapoumeroulie, et al 2005) and ET-3 (Makis, et al 2004), and by affecting the degree of adherence of sickled erythrocytes and leukocytes through decreasing the levels of endothelial adhesion molecules such as sVCAM-1, sICAM-1, sSELE and sSELP (Conran, et al 2004, Kato, et al 2005, Saleh, et al 1999). Hydroxyfasudil has been shown to suppress I/R injury-induced generation of ROS (Shiotani, et al 2004) and at least the levels of vasoconstrictor, ET-1 (Dai, et al 2011); in specific embodiments it also suppresses the level of vasoconstrictor, ET-3. Hydroxyfasudil has also been shown to reduce ICAM-1 expression in diabetes-induced microvascular damage (Arita, et al 2009), as well as reduce ICAM-1, SELE and SELP, thereby diminishing leukocyte-endothelial adhesion in colonic I/R injury (Santen, et al 2010). HU therapy has also been shown to reduce erythrocyte-endothelial adhesion by reducing the gene and protein expression of adhesion molecules such as VLA-4 and CD36 on the surface of erythrocytes (Gambero, et al 2007). However, Hydroxyfasudil has been shown to reduce HIF-1a (Takata, et al 2008), TF (Satoh, et al 2010) and NFκB (He, et al 2008). Additionally, HU therapy decreased levels of inflammatory mediators such as GM-CSF (Conran, et al 2007) and TNF-α, and it has been experimentally shown that HU therapy exert no effect on the levels of IL-8 (Lanaro, et al 2009). However, HU has been shown to increase levels of anti-inflammatory mediator IL-10 (Lanaro, et al 2009), thereby attempting to reduce the inflammatory response but has not been effective. Hydroxyfasudil has been shown to decrease pro-inflammatory mediators such as TNF-α (He, et al 2008), IL-1β (He, et al 2008) and increase the anti-inflammatory mediator IL-10 (Ding, et al 2010).

In certain embodiments of the invention, a compound that induces HbF production is employed alone or with one or more other drugs (some of which may or may not induce HbF production) for the treatment of SCD. The individual may be known to have SCD or is suspected of or at risk for having SCD. The individual may have a family history of SCD. The individual may be known to be a carrier of a mutation that causes SCD or be known to have one or more biological parents that have a mutation that causes SCD. The individual may experience one or more symptoms of SCD, including, for example, fatigue, anemia, pain crises, dactylitis (swelling and inflammation of the hands and/or feet), arthritis, bacterial infections, splenic sequestration, liver congestion, leg ulcers, and so forth.

In embodiments of the invention, Hydroxyfasudil has the advantage over HU that Hydroxyfasudil has the ability to better inhibit pro-inflammatory mediators related to the degree of toxicity. In particular embodiments of the invention, Hydroxyfasudil is employed alone or with one or more other drugs as an alternative drug to reduce at least one symptom of SCD. In specific embodiments, Hydroxyfasudil is employed with HU for the treatment of SCD. In embodiments wherein Hydroxyfasudil is utilized with at least one other compound, those two or more other compounds may work additively or synergistically with Hydroxyfasudil.

Treatment with methods and/or compositions of the invention may begin in the first year of life. Treatment may begin for infants or younger children, for example those suffering with fever, abdominal pain, bacterial infections (including pneumococcal bacterial infections), painful swellings of the hands and feet (dactylitis), and/or splenic sequestration. Treatment may begin for adolescents and young adults, including, for example, those that develop leg ulcers, aseptic necrosis, and/or eye damage. Treatment may begin in an adult, for example one having intermittent pain episodes due to injury of bone, muscle, and/or internal organs.

The treatment regimen of the invention may include one or more doses for the individual. In some embodiments, dosage levels include a maximum dose of 700 mg/kg and a minimum dosage of 0.5 mg/kg. Dosage levels include 0.5, 1, 10, 20, 25, 30, 40, 50, 60, 75, 80, 90, 100, 110, 120, 130, 140, 150, 160, 170, 175, 180, 190, 200, 210, 220, 230, 240, 250, 260, 270, 275, 280, 290, 300, 310, 320, 330, 340, 350, 360, 370, 375, 380, 390, 400, 410, 420, 430, 440, 450, 460, 470, 475, 480, 490, 500, 510, 520, 530, 540, 550, 560, 570, 575, 580, 590, 600, 610, 620, 630, 640, 650, 660, 670, 675, 680, 690, and 700 mg/kg or at least one of these amounts. Dosage levels may include a range of 0.5-700 mg/kg, 1-700 mg/kg, 10-700 mg/kg, 25-700 mg/kg, 50-700 mg/kg, 75-700 mg/kg, 100-700 mg/kg, 125-700 mg/kg, 150-700 mg/kg, 175-700 mg/kg, 200-700 mg/kg, 225-700 mg/kg, 250-700 mg/kg, 275-700 mg/kg, 300-700 mg/kg, 325-700 mg/kg, 350-700 mg/kg, 375-700 mg/kg, 400-700 mg/kg, 425-700 mg/kg, 450-700 mg/kg, 475-700 mg/kg, 500-700 mg/kg, 525-700 mg/kg, 550-700 mg/kg, 575-700 mg/kg, 600-700 mg/kg, 625-700 mg/kg, 650-700 mg/kg, 675-700 mg/kg, 1-600 mg/kg, 1-500 mg/kg, 1-400 mg/kg, 1-300 mg/kg, 1-200 mg/kg, 1-100 mg/kg, 10-700 mg/kg, 10-600 mg/kg, 10-500 mg/kg, 10-400 mg/kg, 10-300 mg/kg, 10-200 mg/kg, 10-100 mg/kg, 20-700 mg/kg, 20-600 mg/kg, 20-500 mg/kg, 20-400 mg/kg, 20-300 mg/kg, 20-200 mg/kg, 20-150 mg/kg, 20-100 mg/kg, 20-75 mg/kg, 20-50 mg/kg, 30-700 mg/kg, 30-60 mg/kg, 30-500 mg/kg, 30-400 mg/kg, 30-300 mg/kg, 30-200 mg/kg, 30-100 mg/kg, 40-700 mg/kg, 40-600 mg/kg, 40-500 mg/kg, 40-400 mg/kg, 40-300 mg/kg, 40-200 mg/kg, 40-100 mg/kg, 50-700 mg/kg, 50-600 mg/kg, 50-500 mg/kg, 50-400 mg/kg, 50-300 mg/kg, 50-200 mg/kg, 50-100 mg/kg, 60-700 mg/kg, 60-600 mg/kg, 60-500 mg/kg, 60-400 mg/kg, 60-300 mg/kg, 60-200 mg/kg, 60-100 mg/kg, 70-700 mg/kg, 70-600 mg/kg, 70-500 mg/kg, 70-400 mg/kg, 70-300 mg/kg, 70-200 mg/kg, 70-100 mg/kg, 80-700 mg/kg, 80-600 mg/kg, 80-500 mg/kg, 80-400 mg/kg, 80-300 mg/kg, 80-200 mg/kg, 80-100 mg/kg, 90-700 mg/kg, 90-600 mg/kg, 90-500 mg/kg, 90-400 mg/kg, 90-300 mg/kg, 90-200 mg/kg, 90-100 mg/kg, 100-700 mg/kg, 100-600 mg/kg, 100-500 mg/kg, 100-400 mg/kg, 100-300 mg/kg, 100-200 mg/kg, 200-700 mg/kg, 200-600 mg/kg, 200-500 mg/kg, 200-400 mg/kg, 200-300 mg/kg, 300-700 mg/kg, 300-600 mg/kg, 300-500 mg/kg, 300-400 mg/kg, 400-700 mg/kg, 400-600 mg/kg, 400-500 mg/kg, 500-700 mg/kg, 500-600 mg/kg, 600-700 mg/kg, or any range therebetween.

Multiple doses of one or a combination of drugs may be delivered to the individual periodically, such as one or more times a day, one or more times a week, or one or more times a month, for example. The delivery may be oral, intravenous, subcutaneous, for example, or by other means. The compound of the invention may be delivered as a solid or as a liquid and may require the individual to ingest the compound with food or shortly after ingesting food.

In embodiments of the invention, an individual is diagnosed with sickle cell disease prior to receiving the inventive treatment. Sickle cell anemia may be indicated when abnormal sickle-shaped cells in the blood are identified, such as microscopically. Testing may alternatively or additionally include examining a smear of blood using a special low-oxygen preparation (referred to as a sickle prep). Additional or alternative tests may be utilized, including to detect the abnormal hemoglobin S (such as solubility tests performed on tubes of blood solutions) and/or by specifically quantifying the types of hemoglobin present using a hemoglobin electrophoresis test (identifies the hemoglobins in the blood by separating them). In some cases there is prenatal diagnosis utilizing amniocentesis or chorionic villus sampling, for example, and the sample obtained is then tested for DNA analysis of the fetal cells; infants, adolescents, and/or adults may also be diagnosed with DNA testing for particular mutation(s) that cause sickle cell.

In embodiments of the invention, one or more compounds are delivered to an individual that reduce one or more side effects of a drug employed for SCD. In some embodiments, one or more compounds are delivered to an individual that reduce one or more side effects of HU for the treatment of any medical condition, including SCD. The one or more compounds may or may not be inducers of HbF production, in some embodiments. In specific cases, for example, the one or more compounds (such as hydroxyfasudil, for example) reduces coagulation and/or reduces inflammation in an individual, including an individual that has been or is being or will be administered HU. Such biological effects by hydroxyfasudil, for example, to improve deleterious side effects of HU, for example, may be direct or indirect.

In certain embodiments of the invention, Isocoronarin D is used alone or with one or more other compounds in the treatment and/or prevention of SCD. The Isocoronarin D may be utilized in conjunction with hydroxyfasudil, in certain aspects. In particular embodiments, Isocoronarin D is employed with one or more inducers of HbF production.

In some embodiments, there is a method of treating an individual with sickle cell disease, comprising the step of delivering to the individual a therapeutically effective amount of Hydroxyfasudil. In specific cases, the method is further defined as delivering to the individual a therapeutically effective amount of Hydroxyfasudil and an inducer of fetal hemoglobin (HbF) production. In specific embodiments, the inducer of HbF production is selected from the group consisting of hydroxyurea, isocoronarin D, 5-azacytidine, citarabine, butyrates, tricostatin, apicidin, scripaid, mithramycin, cisplatin, tallimustine, angelicin, rapamycin, everolimus, resveratrol, 5-methoxypsoralen, lenalidomide, pomalidomide, triple-helix oligodeoxynucleotides, peptide nucleic acids, and a combination thereof In certain embodiments, Hydroxyfasudil and the inducer of HbF production are delivered simultaneously or are delivered separately. In cases wherein there is separate delivery of Hydroxyfasudil and the inducer of HbF production, the separate delivery of Hydroxyfasudil and the inducer of HbF production may be delivered within minutes, hours, days, weeks, or months of each other. In cases where more than one compound is delivered to an individual, the delivery of the two compounds may be in the same way or in different ways.

In specific embodiments of the methods, they further comprise the step of determining that the individual has sickle cell disease and/or determining that a biological family member has sickle cell disease.

In some embodiments of the invention, there are methods of treating an individual with sickle cell disease, comprising the step of delivering to the individual a therapeutically effective amount of Isocoronarin D. The methods may be further defined as delivering to the individual a therapeutically effective amount of Isocoronarin D and an inducer of fetal hemoglobin (HbF) production. In some embodiments, the methods further comprise delivering another sickle cell disease treatment to the individual.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description. It is to be expressly understood, however, that the disclosure is provided for the purpose of illustration and description only and is not intended as a definition of the limits of the present invention.

DETAILED DESCRIPTION OF THE INVENTION

I. Definitions

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "inducer of fetal hemoglobin (or HbF) production" as used herein refers to one or more compounds that directly or indirectly increase the level of fetal hemoglobin or one or more subunits thereof, in a mammalian cell, including increasing the transcription or translation of HbF.

The term "therapeutically effective amount" as used herein refers to that amount which, when administered to a subject or patient for treating a disease, is sufficient to effect such treatment for the disease, including to ameliorate at least one symptom of the disease.

II. Certain Embodiments of the Invention

Embodiments of the invention include utilizing Hydroxyfasudil for treatment of SCD, and in specific embodiments Hydroxyfasudil is utilized with one or more other drug compounds. In particular cases Hydroxyfasudil is utilized with HU or with another inducer of HbF production.

Currently, Hydroxyurea (HU) is the only FDA approved drug capable of modifying the SCD processes (Brawley, et al 2008). HU positively counteracts the pathophysiology of SCD by increasing the production of fetal hemoglobin (HbF)-containing erythrocytes via stimulation of the NO-cyclic guanosine monophosphate (cGMP) signaling pathway (Cokic, et al 2003) and indirectly altering gene expression and proteins associated with the pathophysiology of SCD. The increased concentration of HbF-containing erythrocytes dilutes the concentration of sickled erythrocytes thereby sequentially triggering decreased hemolysis (Olnes, et al 2009), increased NO bioavailability (Conran, et al 2004) and decreased endothelium activation (Haynes, et al 2008). However, HU has been demonstrated to reduce leukocyte counts in patients on therapy (Charache, et al 1996).

It has also been demonstrated that HU therapy induces side effect such as inducing DNA damage (Friedrisch, et al 2008), reducing sperm counts (Grigg 2007) and producing iron nitrosyl Hb (Lockamy, et al 2003). It is important to note that HU increases the expression of pro-inflammatory molecules such as IL-6 and IL-8 which contributes to the chronic inflammatory state associated with the pathophysiology of SCD (Laurance, et al 2010). Moreover, HU has no demonstrable effects on the levels of the pro-coagulatory molecule fibronectin that contributes to vaso-occlusion (Saleh, et al 1999). Furthermore, not all SCD patients respond to HU therapy. Therefore, because of the side effects of HU there is a need for less toxic drugs for the treatment of SCD.

In embodiments of the invention, Hydroxyfasudil is combined with one or more inducers of HbF production, and in at least some cases Hydroxyfasudil alone or in combination with others renders a less toxic and more effective treatment for SCD. Such a combination of compounds (which may be synergistic) is beneficial compared to HU treatment because of advantages such as increased HbF production, reduced inflammation and reduced vaso-occlusion, for example.

Although Hydroxyfasudil has demonstrable effects for treating acute ischemic stroke (Shibuya, et al 2005), stable angina (Vicari, et al 2005), cerebral vasospasm (Suzuki, et al 2008), pulmonary hypertension (Doe, et al 2009) and Alzheimer's disease (Huentelman, et al 2009), it has not yet been experimentally proven that Hydroxyfasudil increases HbF production that at least in some cases is useful for SCD therapy and that effect of HU therapy. Useful effects of the inventive use of combination of drugs (in the concentration necessary to bring about the desired beneficial effects in the treated patient) includes the beneficial and distinguishing effects (compared to HU) of relieving vaso-occlusive crisis and/or reducing inflammation.

In specific embodiments of the invention, the required HbF production can be induced by HbF inducers that are less toxic than HU compared to the situation when HU is used alone. To this effect, in some embodiments HU may be used together with Hydroxyfasudil including, for example, in dosages smaller than currently administered. In some embodiments, hydroxyfasudil compensates for known HbF inducers' inability to effectively modulate vaso-occlusion and inflammation associated with the effective treatment of SCD.

Other embodiments of the invention include a Literature Based Discovery (LBD) approach to identify one or more candidate drugs for the treatment of SCD that are more suitable treatment than the currently administered HU therapy.

Exemplary methods are as follows:

1. The inventors used Dragon Knowledge Explorer system to create DESSCD, an LBD tool focused on published scientific literature on SCD and blood diseases. DESSCD allowed generation of hypotheses based on which information was extracted on blood disease drugs (BDDs) linked to specific genes and proteins implicated in the pathophysiology of SCD. In total, 232,634 SCD-related Medline abstracts were processed.

2. The inventors collated the BDDs that had been linked to all the selected SCD-related molecules and proteins.

3. The inventors extracted the BDDs that have not been screened for application as a SCD drug.

4. The inventors hand curated and extracted the BDDs in Step 3 that induced the desired effect on the molecules and proteins implicated in the pathophysiology of SCD.

III. Inducers of HbF Production

One or more inducers of HbF production may be employed in the invention. In specific aspects, the inducer lacks deleterious side effects associated with HU treatment. Exemplary inducers of HbF production include hydroxyurea, isocoronarin D, 5-azacytidine, citarabine, butyrates, tricostatin, apicidin, scriptaid, mithramycin, cisplatin, tallimustine, angelicin, rapamycin, everolimus, resveratrol, 5-methoxypsoralen, lenalidomide, pomalidomide, triple-helix oligodeoxynucleotides, peptide nucleic acids, or a combination thereof (see Gambari and Fibach, 2007; Moutouh-de Parseval et al., 2008; or Bianchi et al., 2007, for example).

Furthermore, in vitro model systems for screening potential inducers of fetal hemoglobin are known in the art. For examples, cells transfected with reporter genes under the control of $^G\gamma$-globin gene promoter may be employed (see Skarpidi et al., 2000, for example). In other cases, one can utilize reporter genes within an intact β-globin gene locus under the $^G\gamma$-globin promoter (see Vadolas et al., 2004, for example).

IV. Combination Therapies

In some embodiments, one or more compounds useful for treating sickle cell disease or enhancing treatment of another sickle cell disease drug compound are employed in the invention. In specific embodiments, hydroxyfasudil is employed with at least one other compound in the treatment of sickle cell disease, and the two or more compounds may act additively or synergistically.

The administration of the two or more SCD drug compounds may be simultaneous or it may be separate. In such instances where it is separate, it is contemplated that one may provide an individual with both compounds within seconds or minutes or days or weeks or months from each other. In some cases, one may provide an individual within about 1-60 minutes of each other or within 1-24 h of each other or within about 6-12 h of each other or within 12-24 h of each other, or within 1-7 days of each other, or within 1-4 weeks of each other or 1-12 months of each other, for example. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

In some cases, there is substantially simultaneous delivery of the multiple compounds. In certain cases, the two or more SCD compounds are delivered in a same route, although in specific cases the two or more SCD compounds are delivered differently (for example, one oral and one by i.v.).

Administration of the therapeutic compounds of the present invention to a patient will follow general protocols for the administration of drugs, taking into account the toxicity, if any, of the drug. It is expected that the treatment cycles would be repeated as necessary. It also is contemplated that various standard therapies for symptoms of sickle cell disease may be applied in combination with hydroxyfasudil and/or other medical treatments (such as pain relievers, antibiotics, oxygen therapy, blood transfusions, and so forth).

V. Pharmaceutical Preparations

Pharmaceutical compositions of the present invention comprise an effective amount of one or more sickle cell disease drug compounds dissolved or dispersed in a pharmaceutically acceptable carrier. In particular embodiments, the pharmaceutical preparation comprises one or more sickle cell disease drugs, including one or more inducers of HbF production. In specific aspects, the kit comprises Hydroxyfasudil and, optionally, another compound including, for example, an inducer of HbF production. In some embodiments, the pharmaceutical preparation comprises Isocoronarin D.

The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one compound or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compound may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compound may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a sickle cell disease drug compound(s), one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compound may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the compound is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the sickle cell disease drug compound may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VI. Kits of the Invention

Any of the compositions described herein may be comprised in a kit. In a non-limiting example, a sickle cell drug compound (s) may be comprised in a kit. In particular embodiments, the kit comprises one or more sickle cell drug compounds, including one or more inducers of HbF production. In specific aspects, the kit comprises hydroxyfasudil and, optionally, another compound including, for example, an inducer of HbF production. In some embodiments, the kit comprises isocoronarin D.

The kits may comprise a suitably aliquoted sickle cell drug compound, lipid and/or additional agent compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the sickle cell drug compound(s) and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition, in which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the invention may also comprise, and/or be packaged with, an instrument for assisting with the injection/administration and/or placement of the ultimate sickle cell drug compound(s) within the body of an animal. Such an instrument may be a syringe, pipette, forceps, and/or any such medically approved delivery vehicle, for example.

EXAMPLES

The following examples are presented in order to more fully illustrate the preferred embodiments of the invention. They should in no way, however, be construed as limiting the broad scope of the invention.

Example 1

Exemplary Identification of SCD Drugs

Current research focuses on disease modifying drugs and curative strategies such as stem cell transplantation (Bernaudin, et al 2007), gene therapy (Sadelain 2006) and Haemoglobin F (HbF)-inducers (Ley, et al 1983), as these are likely to have the most impact on SCD patients. Nonetheless, the morbidity and sequelae of the disease remains high. Efforts toward discovery of disease modifying drugs can be augmented by leveraging the plethora of molecular data in published biomedical literature, as available chemicals with pharmaceutical effect associated with an erythrocyte disease other than SCD may be more suitable candidate for the treatment of SCD than HU. In this endeavor, as of Feb. 28, 2011, 232,634 SCD-related MEDLINE abstracts were retrieved from PubMed, 34.64% (80,574) of which were published in the last decade. This volume of biomedical data cannot be processed by a single researcher or research group in a reasonable time. Thus, the inventors have implemented a text-mining approach that allows for the summarization of this large volume of raw data by automatically distilling the information, extract text, discovering implicit links by association and generating hypotheses. We used a literature based discovery (LBD) tool DES (Dragon Exploration System) to generate hypotheses leading to the identification of chemicals with pharmaceutical effect associated with an erythrocyte disease other than SCD may be more suitable candidate for the treatment of SCD than HU. This methodology allowed for the identification of Hydroxyfasudil as a SCD drug, in certain embodiments. The inventors additionally hand curated the PubMed literature to identify potential SCD drugs that may have been omitted as the methodology only allows for the inclusion of well researched potential SCD drugs.

The Study allowed for the identification of Hydroxyfasudil or Fusadil (5-(1,4-diazepane-1-sulfonyl)isoquinolin-1-ol), a recognized Rho-kinase inhibitor as a potential novel SCD drug. A comparative analysis of Hydroxyurea and Hydroxyfasudil in relation to SCD displays the advantages of using Hydroxyfasudil to treat SCD (Table 6).

TABLE 6

Effects by Hydroxyfasudil (HF) compared to HU related treatment for SCD

| Molecules | Type of molecule | Expression status in SCD | References | Effect of HU | Effect of HF |
|---|---|---|---|---|---|
| ROS | IR injury-related molecule | up | (Huang, et al 2007) | not known | decrease |
| NO | vasodilator | down | (Eberhardt, et al 2003) | increase | increase |
| ET-1 | vasoconstrictor | up | (Werdehoff, et al 1998) | decrease | decrease |
| ET-3 | vasoconstrictor | up | (Makis, et al 2004) | decrease | not known |
| NFkB | Activator of endothelial cells | up | (Belcher, et al 2005) | decrease | decrease |
| HIF-1 | Activator of endothelial cells | up | (Kim, et al 2006) | not known | decrease |
| TF | Activator of endothelial cells | up | (Solovey, et al 1998) | not known | decrease |
| eNOS | Inhibitor of endothelial cell activation | down | (Solovey, et al 2010) | increase | increase |
| TNFα | cytokine/inflammatory | up | (Lanaro, et al 2009) | decrease | decrease |
| IL-1β | cytokine/inflammatory | up | (Wanderer 2009) | increase | decrease |
| IL-8 | chemokine/inflammatory | up | (Lanaro, et al 2009) | increase | not known |
| IL-6 | chemokine/inflammatory | up | (Croizat 1994) | increase | decrease |
| IL-3 | inflammatory | up | (Croizat 1994) | increase | not known |
| GM-CSF | inflammatory | up | (Conran, et al 2007) | decrease | not known |
| IL-10 | Anti-inflammatory | down | (Lanaro et al. 2009) | increase | increase |
| VCAM-1 | adhesion | up | (Solovey, et al 1997) | decrease | not known |

TABLE 6-continued

Effects by Hydroxyfasudil (HF) compared to HU related treatment for SCD

| Molecules | Type of molecule | Expression status in SCD | References | Effect of HU | Effect of HF |
|---|---|---|---|---|---|
| ICAM-1 | adhesion | up | (Solovey, et al 1997) | decrease | decrease |
| SELP | adhesion | up | (Solovey, et al 1997) | decrease | decrease |
| SELE | adhesion | up | (Solovey, et al 1997) | decrease | decrease |
| VLA-4 | adhesion | up | (Gambero, et al 2007) | decrease | not known |
| CD36 | adhesion | up | (Gambero, et al 2007) | decrease | not known |
| FN1 | coagulatory | up | (Saleh et al.1999) | no effect | decrease | increase = increases protein levels
decrease = reduces protein levels
no effect = exert no effect on protein levels
not known = has not been experimentally determined The inventors additionally hand curated the literature to identify potential drugs for the treatment of SCD. Isocoronarin D (Chokchaisiri, et al 2010) was identified as a useful drug in certain embodiments for the treatment of SCD as experimental evidence demonstrates its ability to induce the production of fetal HbF. (see Example 2)

Comparative analysis of HU and Hydroxyfasudil in relation to SCD indicates that Hydroxyfasudil should be combined with inducer(s) of HbF in order to combat SCD more efficiently. Hydroxyfasudil has several distinctive features that HU does not possess that results in reduced vaso-occlusion and reduced inflammation.

Example 2

Isocoronarin D Embodiments

As mentioned above, the effectiveness of HU for the treatment of SCD is a consequence of its ability to produce HbF via stimulation of the NO-cyclic guanosine monophosphate (cGMP) signaling pathway (Cokic, et al 2003). Isocoronarin D induces the production of HbF, however, it also displays the propensity to induce HbF production with little to no associated toxicity.

A PubMed search using keywords "fetal hemoglobin production AND drug NOT sickle cell" retrieved 84 Medline article from which only Isocoronarin D (Chokchaisiri, et al 2010) was identified as a potential drugs for the treatment of SCD as experimental evidence demonstrates its ability to induce the production of fetal HbF that is the primary factor for the effectiveness of HU therapy for SCD.

Methodology:

1. The inventors used compiled based on Dragon Knowledge Exploration System (DKES) the exploration system for SCD, a Literature Based Discovery (LBD) tool focused on literature for SCD and blood diseases to generate hypotheses that allowed teh inventors to extract blood disease drugs (BDDs) that have demonstrated the ability to induce HbF production.

2. The inventors hand curated the BDDs that had been linked to HbF production but have not been screened for application as SCD drugs.

The study allowed for the identification if Isocoronarin D. Isocoronarin D was isolated for the first time from the rhizome of *Hedychium coronarium* (Zingiberaceae), collected in the Kathmandu Valley, Nepal Singh et al., 1991). A study by Chockchaisiri et al. demonstrates HbF production using a K562 reporter cell line harboring the enhanced green fluorescence protein (EGFP) gene under the control of a (G) gamma-globin promoter. In this assay, the reporter cell lines were treated with the known HbF inducers, hemin and cisplatin, and seven diterpenes. Of the seven diterpenes, Isocoronarin D exhibited the highest EGFP inducing potency or HbF production (Chokchaisiri, et al 2010). They also evaluated the degree of cytoxicity associated with the Isocoronarin D-induced HbF production and showed that at optimal concentration for HbF production, Isocoronarin D maintains cell viability of 75-80% (Chockchaisiri et al 2010).

References

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

Patents and Patent Applications

U.S. Pat. No. 5,399,363
U.S. Pat. No. 5,466,468
U.S. Pat. No. 5,543,158
U.S. Pat. No. 5,580,579
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,613,308
U.S. Pat. No. 6,7537,514

Publications

Abraham, E., Brock, E. A., Candela-Lena, J. I., Davies, S. G., Georgiou, M., Nicholson, R. L., Perkins, J. H., Roberts, P. M., Russell, A. J., Sanchez-Fernandez, E. M., Scott, P. M., Smith, A. D. & Thomson, J. E. (2008) Asymmetric synthesis of N,O,O,O-tetra-acetyl d-lyxophytosphingosine, jaspine B (pachastrissamine), 2-epi-jaspine B, and deoxoprosophylline via lithium amide conjugate addition. Org Biomol Chem, 6, 1665-1673.

Arita, R., Hata, Y., Nakao, S., Kita, T., Miura, M., Kawahara, S., Zandi, S., Almulki, L., Tayyari, F., Shimokawa, H., Hafezi-Moghadam, A. & Ishibashi, T. (2009) Rho kinase inhibition by fasudil ameliorates diabetes-induced microvascular damage. Diabetes, 58, 215-226.

Barabino, G. A., Platt, M. O. & Kaul, D. K. (2010) Sickle cell biomechanics. Annu Rev Biomed Eng, 12, 345-367.

Belcher, J. D., Mahaseth, H., Welch, T. E., Otterbein, L. E., Hebbel, R. P. & Vercellotti, G. M. (2006) Heme oxygenase-1 is a modulator of inflammation and vaso-occlusion in transgenic sickle mice. J Clin Invest, 116, 808-816.

Belcher, J. D., Mahaseth, H., Welch, T. E., Vilback, A. E., Sonbol, K. M., Kalambur, V. S., Bowlin, P. R., Bischof, J. C., Hebbel, R. P. & Vercellotti, G. M. (2005) Critical role of endothelial cell activation in hypoxia-induced vasoocclusion in transgenic sickle mice. Am J Physiol Heart Circ Physiol, 288, H2715-2725.

Bernaudin, F., Socie, G., Kuentz, M., Chevret, S., Duval, M., Bertrand, Y., Vannier, J. P., Yakouben, K., Thuret, I., Bordigoni, P., Fischer, A., Lutz, P., Stephan, J. L., Dhedin, N., Plouvier, E., Margueritte, G., Bones, D., Verlhac, S., Esperou, H., Coic, L., Vernant, J. P. & Gluckman, E. (2007) Long-term results of related myeloablative stem-cell transplantation to cure sickle cell disease. Blood, 110, 2749-2756.

Bianchi, N., Zuccato, C., Lampronti, I., Borgatti, M., and Gambari, R. (2007) Fetal Hemoglobin Inducers from the Natural World: A Novel Approach for Identification of Drugs for the Treatment of β-Thalassemia and Sickle-Cell Anemia. eCAM, 6(2): 141-151.

Brawley, O. W., Cornelius, L. J., Edwards, L. R., Gamble, V. N., Green, B. L., Inturrisi, C., James, A. H., Laraque, D., Mendez, M., Montoya, C. J., Pollock, B. H., Robinson, L., Scholnik, A. P. & Schori, M. (2008) National Institutes of Health Consensus Development Conference statement: hydroxyurea treatment for sickle cell disease. Ann Intern Med, 148, 932-938.

Canalli, A. A., Proenca, R. F., Franco-Penteado, C. F., Traina, F., Sakamoto, T. M., Saad, S. T., Conran, N. & Costa, F. F. (2011) Participation of Mac-1, LFA-1 and VLA-4 integrins in the in vitro adhesion of sickle cell disease neutrophils to endothelial layers, and reversal of adhesion by simvastatin. Haematologica, 96, 526-533.

Chada, D., Mather, T. & Nollert, M. U. (2006) The synergy site of fibronectin is required for strong interaction with the platelet integrin alphaIIbbeta3. Ann Biomed Eng, 34, 1542-1552.

Charache, S., Barton, F. B., Moore, R. D., Terrin, M. L., Steinberg, M. H., Dover, G. J., Ballas, S. K., McMahon, R. P., Castro, 0. & Orringer, E. P. (1996) Hydroxyurea and sickle cell anemia. Clinical utility of a myelosuppressive "switching" agent. The Multicenter Study of Hydroxyurea in Sickle Cell Anemia. Medicine (Baltimore), 75, 300-326.

Chiu, J. J., Lee, P. L., Chen, C. N., Lee, C. I., Chang, S. F., Chen, L. J., Lien, S. C., Ko, Y. C., Usami, S. & Chien, S. (2004) Shear stress increases ICAM-1 and decreases VCAM-1 and E-selectin expressions induced by tumor necrosis factor-[alpha] in endothelial cells. Arterioscler Thromb Vasc Biol, 24, 73-79.

Chokchaisiri, R., Chaneiam, N., Svasti, S., Fucharoen, S., Vadolas, J. & Suksamrarn, A. (2010) Labdane diterpenes from the aerial parts of Curcuma comosa enhance fetal hemoglobin production in an erythroid cell line. J Nat Prod, 73, 724-728.

Cokic, V. P., Smith, R. D., Beleslin-Cokic, B. B., Njoroge, J. M., Miller, J. L., Gladwin, M. T. & Schechter, A. N. (2003) Hydroxyurea induces fetal hemoglobin by the nitric oxide-dependent activation of soluble guanylyl cyclase. J Clin Invest, 111, 231-239.

Conran, N., Oresco-Santos, C., Acosta, H. C., Fattori, A., Saad, S. T. & Costa, F. F. (2004) Increased soluble guanylate cyclase activity in the red blood cells of sickle cell patients. Br J Haematol, 124, 547-554.

Conran, N., Saad, S. T., Costa, F. F. & Ikuta, T. (2007) Leukocyte numbers correlate with plasma levels of granulocyte-macrophage colony-stimulating factor in sickle cell disease. Ann Hematol, 86, 255-261.

Croizat, H. (1994) Circulating cytokines in sickle cell patients during steady state. Br J Haematol, 87, 592-597.

Dai, Z. K., Wu, B. N., Chen, I. C., Chai, C. Y., Wu, J. R., Chou, S. H., Yeh, J. L., Chen, I. J. & Tan, M. S. (2011) Attenuation of pulmonary hypertension secondary to left ventricular dysfunction in the rat by Rho-kinase inhibitor fasudil. Pediatr Pulmonol, 46, 45-59.

Devi, S., Kuligowski, M. P., Kwan, R. Y., Westein, E., Jackson, S. P., Kitching, A. R. & Hickey, M. J. (2010) Platelet recruitment to the inflamed glomerulus occurs via an alphaIIbbeta3/GPVI-dependent pathway. Am J Pathol, 177, 1131-1142.

Ding, J., Li, Q. Y., Wang, X., Sun, C. H., Lu, C. Z. & Xiao, B. G. (2010) Fasudil protects hippocampal neurons against hypoxia-reoxygenation injury by suppressing microglial inflammatory responses in mice. J Neurochem, 114, 1619-1629.

Eberhardt, R. T., McMahon, L., Duffy, S. J., Steinberg, M. H., Perrine, S. P., Loscalzo, J., Coffman, J. D. & Vita, J. A. (2003) Sickle cell anemia is associated with reduced nitric oxide bioactivity in peripheral conduit and resistance vessels. Am J Hematol, 74, 104-111.

Ergul, S., Brunson, C. Y., Hutchinson, J., Tawfik, A., Kutlar, A., Webb, R. C. & Ergul, A. (2004) Vasoactive factors in sickle cell disease: in vitro evidence for endothelin-1-mediated vasoconstriction. Am J Hematol, 76, 245-251.

Ferry, A. E., Baliga, S. B., Monteiro, C. & Pace, B. S. (1997) Globin gene silencing in primary erythroid cultures. An inhibitory role for interleukin-6. J Biol Chem, 272, 20030-20037.

Frenette, P. S. (2002) Sickle cell vaso-occlusion: multistep and multicellular paradigm. Curr Opin Hematol, 9, 101-106.

Frenette, P. S. & Atweh, G. F. (2007) Sickle cell disease: old discoveries, new concepts, and future promise. J Clin Invest, 117, 850-858.

Friedrisch, J. R., Pra, D., Maluf, S. W., Bittar, C. M., Mergener, M., Pollo, T., Kayser, M., da Silva, M. A., Henriques, J. A. & da Rocha Silla, L. M. (2008) DNA damage in blood leukocytes of individuals with sickle cell disease treated with hydroxyurea. Mutat Res, 649, 213-220.

Galley, H. F. & Webster, N. R. (2004) Physiology of the endothelium. Br J Anaesth, 93, 105-113.

Gambari, R. and Fibach, E. (2007) Medicinal Chemistry of Fetal Hemoglobin Inducers for Treatment of β-Thalassemia. Curr. Medic. Chem., 14:199-212.

Gambero, S., Canalli, A. A., Traina, F., Albuquerque, D. M., Saad, S. T., Costa, F. F. & Conran, N. (2007) Therapy with hydroxyurea is associated with reduced adhesion molecule gene and protein expression in sickle red cells with a concomitant reduction in adhesive properties. Eur J Haematol, 78, 144-151.

Grigg, A. (2007) Effect of hydroxyurea on sperm count, motility and morphology in adult men with sickle cell or myeloproliferative disease. Intern Med J, 37, 190-192.

Haynes, J., Jr., Obiako, B., Hester, R. B., Baliga, B. S. & Stevens, T. (2008) Hydroxyurea attenuates activated neutrophil-mediated sickle erythrocyte membrane phosphatidylserine exposure and adhesion to pulmonary vascular endothelium. Am J Physiol Heart Circ Physiol, 294, H379-385.

Hidalgo, A., Chang, J., Jang, J. E., Peired, A. J., Chiang, E. Y. & Frenette, P. S. (2009) Heterotypic interactions enabled by polarized neutrophil microdomains mediate thromboinflammatory injury. Nat Med, 15, 384-391.

Huang, G. S., Lopez-Barcons, L., Freeze, B. S., Smith, A. B., 3rd, Goldberg, G. L., Horwitz, S. B. & McDaid, H. M. (2006) Potentiation of taxol efficacy and by discodermolide in ovarian carcinoma xenograft-bearing mice. Clin Cancer Res, 12, 298-304.

Huang, X., Shao, N., Palani, A., Aslanian, R. & Buevich, A. (2007) The total synthesis of psymberin. Org Lett, 9, 2597-2600.

Ingram, V. M. (1957) Gene mutations in human haemoglobin: the chemical difference between normal and sickle cell haemoglobin. Nature, 180, 326-328.

Kaul, D. K., Liu, X. D., Choong, S., Belcher, J. D., Vercellotti, G. M. & Hebbel, R. P. (2004) Anti-inflammatory therapy ameliorates leukocyte adhesion and microvascular flow abnormalities in transgenic sickle mice. Am J Physiol Heart Circ Physiol, 287, H293-301.

Kim, K. S., Rajagopal, V., Gonsalves, C., Johnson, C. & Kalra, V. K. (2006) A novel role of hypoxia-inducible factor in cobalt chloride- and hypoxia-mediated expression of IL-8 chemokine in human endothelial cells. J Immunol, 177, 7211-7224.

Lanaro, C., Franco-Penteado, C. F., Albuqueque, D. M., Saad, S. T., Conran, N. & Costa, F. F. (2009) Altered levels of cytokines and inflammatory mediators in plasma and leukocytes of sickle cell anemia patients and effects of hydroxyurea therapy. J Leukoc Biol, 85, 235-242.

Lapoumeroulie, C., Benkerrou, M., Odievre, M. H., Ducrocq, R., Brun, M. & Elion, J. (2005) Decreased plasma endothelin-1 levels in children with sickle cell disease treated with hydroxyurea. Haematologica, 90, 401-403.

Lee, S. P., Ataga, K. I., Orringer, E. P., Phillips, D. R. & Parise, L. V. (2006) Biologically active CD40 ligand is elevated in sickle cell anemia: potential role for platelet-mediated inflammation. Arterioscler Thromb Vasc Biol, 26, 1626-1631.

Ley, T. J., DeSimone, J., Noguchi, C. T., Turner, P. H., Schechter, A. N., Heller, P. & Nienhuis, A. W. (1983) 5-Azacytidine increases gamma-globin synthesis and reduces the proportion of dense cells in patients with sickle cell anemia. Blood, 62, 370-380.

Lin, F. L., Hsu, J. L., Chou, C. H., Wu, W. J., Chang, C. I. & Liu, H. J. (2011) Activation of p38 MAPK by damnacanthal mediates apoptosis in SKHep 1 cells through the DR5/TRAIL and TNFR1/TNF-alpha and p53 pathways. Eur J Pharmacol, 650, 120-129.

Lockamy, V. L., Huang, J., Shields, H., Ballas, S. K., King, S. B. & Kim-Shapiro, D. B. (2003) Urease enhances the formation of iron nitrosyl hemoglobin in the presence of hydroxyurea. Biochim Biophys Acta, 1622, 109-116.

Lomakina, E. B. & Waugh, R. E. (2010) Signaling and Dynamics of Activation of LFA-1 and Mac-1 by Immobilized IL-8. Cell Mol Bioeng, 3, 106-116.

Makis, A. C., Hatzimichael, E. C., Kolios, G. & Bourantas, K. L. (2004) Circulating endothelin-3 levels in patients with sickle cell disease during hydroxyurea treatment. Haematologica, 89, 360-361.

Miguel, L. I., Almeida, C. B., Traina, F., Canalli, A. A., Dominical, V. M., Saad, S. T., Costa, F. F. & Conran, N. (2011) Inhibition of phosphodiesterase 9A reduces cytokine-stimulated in vitro adhesion of neutrophils from sickle cell anemia individuals. Inflamm Res.

Modell, B. & Darlison, M. (2008) Global epidemiology of haemoglobin disorders and derived service indicators. Bull World Health Organ, 86, 480-487.

Mozzarelli, A., Hofrichter, J. & Eaton, W. A. (1987) Delay time of hemoglobin S polymerization prevents most cells from sickling in vivo. Science, 237, 500-506.

Musa, B. O., Onyemelukwe, G. C., Hambolu, J. O., Mamman, A. I. & Isa, A. H. (2010) Pattern of serum cytokine expression and T-cell subsets in sickle cell disease patients in vaso-occlusive crisis. Clin Vaccine Immunol, 17, 602-608.

Nath, K. A., Grande, J. P., Croat, A. J., Frank, E., Caplice, N. M., Hebbel, R. P. & Katusic, Z. S. (2005) Transgenic sickle mice are markedly sensitive to renal ischemia-reperfusion injury. Am J Pathol, 166, 963-972.

Oh, S. O., Ibe, B. O., Johnson, C., Kurantsin-Mills, J. & Raj, J. U. (1997) Platelet-activating factor in plasma of patients with sickle cell disease in steady state. J Lab Clin Med, 130, 191-196.

Olnes, M., Chi, A., Haney, C., May, R., Minniti, C., Taylor, J. t. & Kato, G. J. (2009) Improvement in hemolysis and pulmonary arterial systolic pressure in adult patients with sickle cell disease during treatment with hydroxyurea. Am J Hematol, 84, 530-532.

Osarogiagbon, U. R., Choong, S., Belcher, J. D., Vercellotti, G. M., Paller, M. S. & Hebbel, R. P. (2000) Reperfusion injury pathophysiology in sickle transgenic mice. Blood, 96, 314-320.

Otterbein, L. E., Soares, M. P., Yamashita, K. & Bach, F. H. (2003) Heme oxygenase-1: unleashing the protective properties of heme. Trends Immunol, 24, 449-455.

Phelan, M., Perrine, S. P., Brauer, M. & Faller, D. V. (1995) Sickle erythrocytes, after sickling, regulate the expression of the endothelin-1 gene and protein in human endothelial cells in culture. J Clin Invest, 96, 1145-1151.

Radi, R., Beckman, J. S., Bush, K. M. & Freeman, B. A. (1991) Peroxynitrite-induced membrane lipid peroxidation: the cytotoxic potential of superoxide and nitric oxide. Arch Biochem Biophys, 288, 481-487.

Rajan, S., Ye, J., Bai, S., Huang, F. & Guo, Y. L. (2008) NF-kappaB, but not p38 MAP kinase, is required for TNF-alpha-induced expression of cell adhesion molecules in endothelial cells. J Cell Biochem, 105, 477-486.

Reiter, C. D. & Gladwin, M. T. (2003) An emerging role for nitric oxide in sickle cell disease vascular homeostasis and therapy. Curr Opin Hematol, 10, 99-107.

Remington's Pharmaceutical Sciences, 18th Ed. Mack Printing Company, 1990.

Sadelain, M. (2006) Recent advances in globin gene transfer for the treatment of beta-thalassemia and sickle cell anemia. Curr Opin Hematol, 13, 142-148.

Saleh, A. W., Hillen, H. F. & Duits, A. J. (1999) Levels of endothelial, neutrophil and platelet-specific factors in sickle cell anemia patients during hydroxyurea therapy. Acta Haematol, 102, 31-37.

Santen, S., Wang, Y., Laschke, M. W., Menger, M. D., Jeppsson, B. & Thorlacius, H. (2010) Rho-kinase signalling regulates CXC chemokine formation and leukocyte recruitment in colonic ischemia-reperfusion. Int J Colorectal Dis, 25, 1063-1070.

Satoh, S., Hitomi, A., Ikegaki, I., Kawasaki, K., Nakazono, O., Iwasaki, M., Mohri, M. & Asano, T. (2010) Amelioration of endothelial damage/dysfunction is a possible mechanism for the neuroprotective effects of Rho-kinase inhibitors against ischemic brain damage. Brain Res Bull, 81, 191-195.

Segers, V. F., Van Riet, I., Andries, L. J., Lemmens, K., Demolder, M. J., De Becker, A. J., Kockx, M. M. & De Keulenaer, G. W. (2006) Mesenchymal stem cell adhesion to cardiac microvascular endothelium: activators and mechanisms. Am J Physiol Heart Circ Physiol, 290, H1370-1377.

Shiotani, S., Shimada, M., Suehiro, T., Soejima, Y., Yosizumi, T., Shimokawa, H. & Maehara, Y. (2004) Involvement of Rho-kinase in cold ischemia-reperfusion injury after liver transplantation in rats. Transplantation, 78, 375-382.

Skarpidi, E., Vassilopoulos, G., Li, Q., Stamatoyannopoulos, G. Blood, 200-, 96, 321.

Solovey, A., Gui, L., Key, N. S. & Hebbel, R. P. (1998) Tissue factor expression by endothelial cells in sickle cell anemia. J Clin Invest, 101, 1899-1904.

Solovey, A., Kollander, R., Milbauer, L. C., Abdulla, F., Chen, Y., Kelm, R. J., Jr. & Hebbel, R. P. (2010) Endothelial nitric oxide synthase and nitric oxide regulate endothelial tissue factor expression in vivo in the sickle transgenic mouse. Am J Hematol, 85, 41-45.

Solovey, A., Lin, Y., Browne, P., Choong, S., Wayner, E. & Hebbel, R. P. (1997) Circulating activated endothelial cells in sickle cell anemia. N Engl J Med, 337, 1584-1590.

Steinberg, M. H. (2008) Sickle cell anemia, the first molecular disease: overview of molecular etiology, pathophysiology, and therapeutic approaches. ScientificWorldJournal, 8, 1295-1324.

Sultana, C., Shen, Y., Rattan, V., Johnson, C. & Kalra, V. K. (1998) Interaction of sickle erythrocytes with endothelial cells in the presence of endothelial cell conditioned medium induces oxidant stress leading to transendothelial migration of monocytes. Blood, 92, 3924-3935.

Takata, K., Morishige, K., Takahashi, T., Hashimoto, K., Tsutsumi, S., Yin, L., Ohta, T., Kawagoe, J., Takahashi, K. & Kurachi, H. (2008) Fasudil-induced hypoxia-inducible factor-1alpha degradation disrupts a hypoxia-driven vascular endothelial growth factor autocrine mechanism in endothelial cells. Mol Cancer Ther, 7, 1551-1561.

Taylor, S., Shacks, S. & Qu, Z. (2001) Effect of anti-IL-6 and anti-10 monoclonal antibodies on the suppression of the normal T lymphocyte mitogenic response by steady state sickle cell disease sera. Immunol Invest, 30, 209-219.

Thomas, T. R., Kavlekar, D. P. & LokaBharathi, P. A. (2010) Marine drugs from sponge-microbe association—a review. Mar Drugs, 8, 1417-1468.

Tsukamoto, S., Kawabata, T., Kato, H., Ohta, T., Rotinsulu, H., Mangindaan, R. E., van Soest, R. W., Ukai, K., Kobayashi, H. & Namikoshi, M. (2007) Naamidines H and I, cytotoxic imidazole alkaloids from the Indonesian marine sponge Leucetta chagosensis. J Nat Prod, 70, 1658-1660.

Turhan, A., Weiss, L. A., Mohandas, N., Coller, B. S. & Frenette, P. S. (2002) Primary role for adherent leukocytes in sickle cell vascular occlusion: a new paradigm. Proc Natl Acad Sci USA, 99, 3047-3051.

Vadolas, J., Wardan, H., Orford, M., Williamson, R., Ioannou, P. A. (2004), 13:223.

van Gils, J. M., Zwaginga, J. J. & Hordijk, P. L. (2009) Molecular and functional interactions among monocytes, platelets, and endothelial cells and their relevance for cardiovascular diseases. J Leukoc Biol, 85, 195-204.

Vilas-Boas, W., Cerqueira, B. A., Zanette, A. M., Reis, M. G., Barral-Netto, M. & Goncalves, M. S. (2010) Arginase levels and their association with Th17-related cytokines, soluble adhesion molecules (sICAM-1 and sVCAM-1) and hemolysis markers among steady-state sickle cell anemia patients. Ann Hematol, 89, 877-882.

Wanderer, A. A. (2009) Rationale for IL-1beta targeted therapy for ischemia-reperfusion induced pulmonary and other complications in sickle cell disease. J Pediatr Hematol Oncol, 31, 537-538.

Werdehoff, S. G., Moore, R. B., Hoff, C. J., Fillingim, E. & Hackman, A. M. (1998) Elevated plasma endothelin-1 levels in sickle cell anemia: relationships to oxygen saturation and left ventricular hypertrophy. Am J Hematol, 58, 195-199.

Westwick, J., Watson-Williams, E. J., Krishnamurthi, S., Marks, G., Ellis, V., Scully, M. F., White, J. M. & Kakkar, V. V. (1983) Platelet activation during steady state sickle cell disease. J Med, 14, 17-36.

Wun, T., Cordoba, M., Rangaswami, A., Cheung, A. W. & Paglieroni, T. (2002) Activated monocytes and platelet-monocyte aggregates in patients with sickle cell disease. Clin Lab Haematol, 24, 81-88.

Wun, T., Paglieroni, T., Field, C. L., Welborn, J., Cheung, A., Walker, N. J. & Tablin, F. (1999) Platelet-erythrocyte adhesion in sickle cell disease. J Investig Med, 47, 121-127.

Yoong, W. C., Tuck, S. M., Pasi, K. J., Owens, D. & Perry, D. J. (2003) Markers of platelet activation, thrombin generation and fibrinolysis in women with sickle cell disease: effects of differing forms of hormonal contraception. Eur J Haematol, 70, 310-314.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating an individual with sickle cell disease, comprising the step of delivering to the individual a therapeutically effective amount of Isocoronarin D.

2. The method of claim 1, further defined as delivering to the individual a therapeutically effective amount of Isocoronarin D and an inducer of fetal hemoglobin (HbF) production.

3. The method of claim 1, further comprising delivering to the individual another sickle cell disease treatment selected from the group consisting of pain relievers, antibiotics, oxygen therapy, and blood transfusions.

* * * * *